US012691094B2

(12) United States Patent
Zhang et al.

(10) Patent No.: US 12,691,094 B2
(45) Date of Patent: Jul. 28, 2026

(54) USE OF CRASSIFOLIN A IN PREPARATION OF DRUG FOR PROMOTING MITOPHAGY AND TREATING NEURODEGENERATIVE DISEASES

(71) Applicant: JINAN UNIVERSITY, Guangzhou (CN)

(72) Inventors: Yubo Zhang, Guangzhou (CN); Fei Xiao, Guangzhou (CN); Guocai Wang, Guangzhou (CN); Evandro Fei Fang, Shanghai (CN); Junping Pan, Guangzhou (CN)

(73) Assignee: JINAN UNIVERSITY, Guangzhou (CN)

( * ) Notice: Subject to any disclaimer, the term of this patent is extended or adjusted under 35 U.S.C. 154(b) by 400 days.

(21) Appl. No.: 18/264,421

(22) PCT Filed: Jun. 22, 2022

(86) PCT No.: PCT/CN2022/100287
§ 371 (c)(1),
(2) Date: Aug. 6, 2023

(87) PCT Pub. No.: WO2023/279957
PCT Pub. Date: Jan. 12, 2023

(65) Prior Publication Data

US 2024/0299342 A1 Sep. 12, 2024

(30) Foreign Application Priority Data

Jul. 9, 2021 (CN) ........................ 202110779308.0

(51) Int. Cl.
*A61K 31/365* (2006.01)
*A61P 25/28* (2006.01)

(52) U.S. Cl.
CPC ............ *A61K 31/365* (2013.01); *A61P 25/28* (2018.01)

(58) Field of Classification Search
CPC .............................. A61K 31/365; A61P 25/28
See application file for complete search history.

(56) References Cited

FOREIGN PATENT DOCUMENTS

| | | | |
|---|---|---|---|
| CN | 110208515 | 9/2019 | |
| CN | 110294723 | 10/2019 | |
| CN | 111904958 | 11/2020 | |
| CN | 113476441 | 10/2021 | |
| CN | 113476441 A * | 10/2021 | ........... A61K 31/352 |
| WO | 2020262971 | 12/2020 | |

OTHER PUBLICATIONS

CN 113476441 A Machine translation (Year: 2021).*
Qui et al. New clerodane diterpenoids from Croton crassifolius, Fitoterapia, Jan. 2016, pp. 81-86 (Year: 2016).*
Qiu, Maosong et al., "Simultaneous determination of six terpenoids in Crotonis Crassifolii Radix by HPLC", Chinese Traditional and Herbal Drugs, vol. 47, No. 21, Nov. 30, 2016 (Nov. 30, 2016).
Liu, Junli et al., "Chemical constituents from Croton crassifolius Geisel", Journal of Chinese Pharmaceutical Sciences, vol. 25, No. 11, Dec. 31, 2016 (Dec. 31, 2016).

* cited by examiner

*Primary Examiner* — Sarah Pihonak
*Assistant Examiner* — Mikhail O'Donnel Robinson
(74) *Attorney, Agent, or Firm* — JMB Davis Ben-David

(57) ABSTRACT

Disclosed in the present invention is the use of Crassifolin A in promoting mitophagy and treating neurodegenerative diseases. According to the present invention, experiments show that the diterpene compound Crassifolin A can significantly increase mitophagy levels, promote the removal of damaged mitochondria, maintain homeostasis in cells, and has potential effects of treating neurodegenerative diseases and other related diseases; moreover, Crassifolin A is a small-molecule compound that can easily penetrate through the blood-brain barrier to reach the brain so as to play a role, can be extracted from a Thickleaf croton root medicinal material, has the advantages of abundant medicinal sources, easy availability, low drug toxicity and few side effects, and has a good application prospect in the treatment of neurodegenerative diseases.

6 Claims, 3 Drawing Sheets

USE OF CRASSIFOLIN A IN PREPARATION OF DRUG FOR PROMOTING MITOPHAGY AND TREATING NEURODEGENERATIVE DISEASES

CROSS-REFERENCE TO RELATED APPLICATIONS

This is the U.S. National Stage of International Patent Application No. PCT/CN2022/100287 filed on Jun. 22, 2022, which claims priority to Chinese Patent Application No. 202110779308.0 filed on Jul. 9, 2021.

TECHNICAL FIELD

The present invention belongs to the field of medicine, and particularly relates to the use of Crassifolin A in promoting mitophagy and treating neurodegenerative diseases.

BACKGROUND

Neurodegenerative diseases (ND) are a type of disease caused by the progressive loss of neuronal structure or function in the body, including Alzheimer's disease (AD), Parkinson's disease (PD), Huntington's disease (HD), amyotrophic lateral sclerosis (ALS), etc. The pathogenesis of such diseases is not yet clear, and there is no effective means for cure. The main pathogenesis hypotheses include the cholinergic theory, the beta-amyloid (Aβ) toxicity theory, the oxidative stress theory, and the tau protein hyperphosphorylation theory. There are two more widely recognized pathogenesis theories for AD. The first is the Aβ toxicity theory, according to which amyloid precursor protein (APP) is sheared into Aβ by β-secretase, which excessively deposited to form senile plaques. The second is the tau protein hyperphosphorylation theory, which consists of the hyperphosphorylation of tau proteins. Hyperphosphorylated tau proteins lose their ability to bind to microtubules, and aggregate into neurofibrillary tangles (NFTs), leading to neuronal degeneration and apoptosis. Currently, there are many studies related to AD other therapy targets, such as glial cells, mitochondria, cellular metabolism, inflammation, etc. In recent years, the research on the relationship between cellular autophagy, neurodegenerative diseases, and tumors has become a hot spot, providing new target sites of drugs for the treatment of neurodegenerative diseases.

Cellular autophagy, also known as "type II cell death", is a process in which cells use, under the regulation of an autophagy-related gene (Atg), lysosomes to degrade their own damaged organelles and macromolecular substances. Currently, three types of autophagy are defined. (1) The first process is called "macro-autophagy", in which vesicles with bilayer membrane wrap cytoplasmic structures to form autophagosomes. Then, the vesicles fuse with lysosomes to form autophagic lysosomes to finally degrade the content.

(2) The second process is called "micro-autophagy", in which the membrane of lysosomes, due to invagination, directly encapsulates the cytoplasmic elements to degrade them inside.

The last process (3) is called molecular chaperone-mediated autophagy-CMA, in which an intracellular target protein is recognized by a molecular chaperone protein. After that, the target and the chaperone proteins form a complex, to be subsequently recognized by a lysosomal-associated membrane protein 2A (LAMP-2A), a receptor on the lysosomal membrane. Finally, the molecular complex translocated to the lumen of the lysosome is degraded.

The involvement of cellular autophagy in the occurrence and development of many diseases is one of the current hot topics in the field of biomedicine. Induction or inhibition of autophagy may play an important role in treatment of disease. The study of mitochondrial diseases is also linked to autophagy. Accumulation of proteins and damaged mitochondria, which ultimately lead to neuronal degeneration, were previously thought to be the etiology of neurodegenerative diseases (e.g. AD). Therefore, inducing the occurrence of cellular autophagy and removing damaged mitochondria may be of great help in improving the symptoms of AD, as well as a potential therapeutic target for drug action in the treatment of AD. At present, the main autophagy inducers are Bredeldin A/Thapsigargin, Carbamazepine/L-690, 330/LithiumChloride (lithium chloride), Earle's balanced salt solution, N-Acetyl-D-sphingosine (C2-ceramide), Rapamycin, and Xestospongin B/C. Existing autophagy inducers act only on a specific process in an autophagic signaling pathway, which makes them clearly inadequate to target a complex autophagic signaling pathway. Therefore, the research for new autophagy inducers has a potential application prospect in the treatment of neurodegenerative diseases.

Crassifolin A (JGX-1) is a diterpene compound isolated from *Croton crassifolius* Geisel., a plant of *Croton* genus in the family of Euphorbiaceae, with the following chemical structural formula:

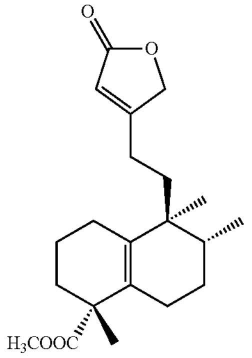

Currently, there are no reports related to the role of Crassifolin A(JGX-1) as an autophagy inducer and in application of neurodegenerative diseases.

SUMMARY

A primary objective of the present invention is to overcome the shortcomings and deficiencies of the prior art, and to provide a use of Crassifolin A in promoting cellular mitophagy in vitro.

Another objective of the present invention is to provide the use of Crassifolin A in the preparation of a mitophagy inducer.

A further objective of the present invention is to provide a use of Crassifolin A in the preparation of a drug for treating neurodegenerative diseases.

The objectives of the present invention are achieved through the following technical solutions.

A use of Crassifolin A (JGX-1) in promoting cellular mitophagy in vitro is provided.

Crassifolin A (JGX-1) has the following chemical structural formula as shown in Formula (I):

Formula (I)

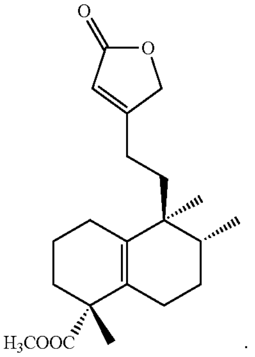

A effective concentration of Crassifolin A is 5-15 μmol/L, preferably 10 μmol/L.

A use of Crassifolin A in the preparation of a mitophagy inducer is provided.

A effective concentration of Crassifolin A is 5-15 μmol/L, preferably 10 μmol/L.

A use of Crassifolin A in the preparation of a drug for treating neurodegenerative diseases is provided.

Crassifolin A can promote mitophagy (increase mitophagy level) and inhibit the expression of phosphorylated Tau, thereby achieving the objective of treating neurodegenerative diseases.

The neurodegenerative diseases include at least one of Alzheimer's disease (AD), Parkinson's disease (PD), Huntington's disease (HD), amyotrophic lateral sclerosis (ALS), different types of spinal cerebellar ataxia, Pick's disease, cerebral ischemia (CI), brain injury (BI), and epilepsy.

The present invention has the following advantages and effects with respect to the prior art.

(1) The present invention discovers a diterpene compound Crassifolin A (JGX-1), which can significantly increase the mitophagy level, promote the removal of damaged mitochondria, maintain homeostasis in cells, and have potential effects of treating neurodegenerative diseases and other related diseases, having a good application prospect in the treatment of neurodegenerative diseases.

(2) The diterpene compound Crassifolin A (JGX-1) of the present invention is a small-molecule compound that can easily penetrate through the blood-brain barrier to reach the brain so as to play a role, significantly increasing the mitophagy level.

(3) The diterpene compound Crassifolin A (JGX-1) of the present invention does not cause mitochondrial apoptosis while enhancing mitophagy, and can be used in drug development for diseases caused by autophagic dysfunction, providing a potential therapeutic drug for neurodegenerative diseases.

(4) The diterpene compound Crassifolin A (JGX-1) of the present invention can be extracted from the roots of *Croton crassifolius*, and has the advantages of abundant medicinal sources, easy availability, low drug toxicity and few side effects.

DETAILED DESCRIPTION OF EMBODIMENTS

The present invention will be further described below in detail with reference to Examples, but the embodiments of the present invention are not limited thereto. Unless otherwise specified, the reagents, methods, and equipments employed in the present invention are conventional reagents, methods, and equipments in this technical field. The testing methods that do not indicate specific experimental conditions in the following Examples are usually performed under conventional experimental conditions or the experimental conditions recommended by the manufacturer. Unless otherwise stated, the reagents and raw materials used in the present invention are commercially available.

Crassifolin A (JGX-1) involved in Examples of the present invention is a diterpene compound, and has the following chemical structural formula as shown in Formula (I). It can be obtained by referring to the literature (Li Jiagui, *Study on Chemical Constituents of Croton crassifolius Geisel* [D], Jinan University, 2013), or can be isolated from *Croton crassifolius* Geisel, a plant of *Croton* genus in the family of Euphorbiaceae.

Formula (I)

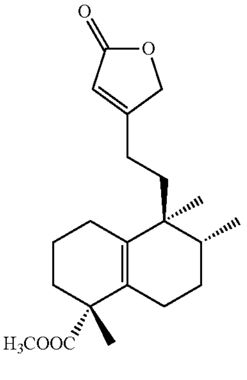

The Hela cells and hSY5Y cells involved in Examples of the present invention are purchased from ATCC.

Example 1

(1) Flow Cytometry of Hela-Mt-Keima Cells for Screening a Mitophagy Drug

The Keima fluorescent protein derived from anthozoan has a pH value-dependent bimodal excitation spectrum, that is, Keima can be excited to emit green fluorescence at neutral pH and acidic pH and red fluorescence under the excitation of light with a wavelength of 440 nm and 586 nm, respectively. Since mitochondria that undergo autophagy eventually enter acidic lysosomes, Keima with the mitochondrial localization (mitocondrial Keima, mt-Keima) can indicate the mitochondria that enter the lysosomes via the autophagic pathway. The specific procedure of this experiment is as follow:

Inoculation of Hela-mt-Keima cells into a 24-well plate at a density of $5\times10^4$, and then adding 1 mL of DMEM medium containing 10% (v/v) fetal bovine serum (FBS) to them to culture for 24 h; after 24 h, respectively adding 0.1% (v/v) DMSO (dimethyl sulfoxide), with DMSO (10 μM) as a solvent control group (DMSO), 10 μM of mitochondrial uncoupling agent (FCCP) (sigma) as a positive drug control group, and 10 μM JGX-1+10 μM FCCP as an experimental group, each group having 3 replicates; collecting cells on the third day by centrifugation at 1000×g for 3 min, resuspending in 0.5 mL of PBS buffer, sieving at 40 μm on the machine, collecting $5\times10^4$ cells by flow cytometry, recording the collection time, 405 nm/Qdot605-A, 561 nm/PE-Texas Red-A, and calculating MI=561/405+561.

Figure 1:
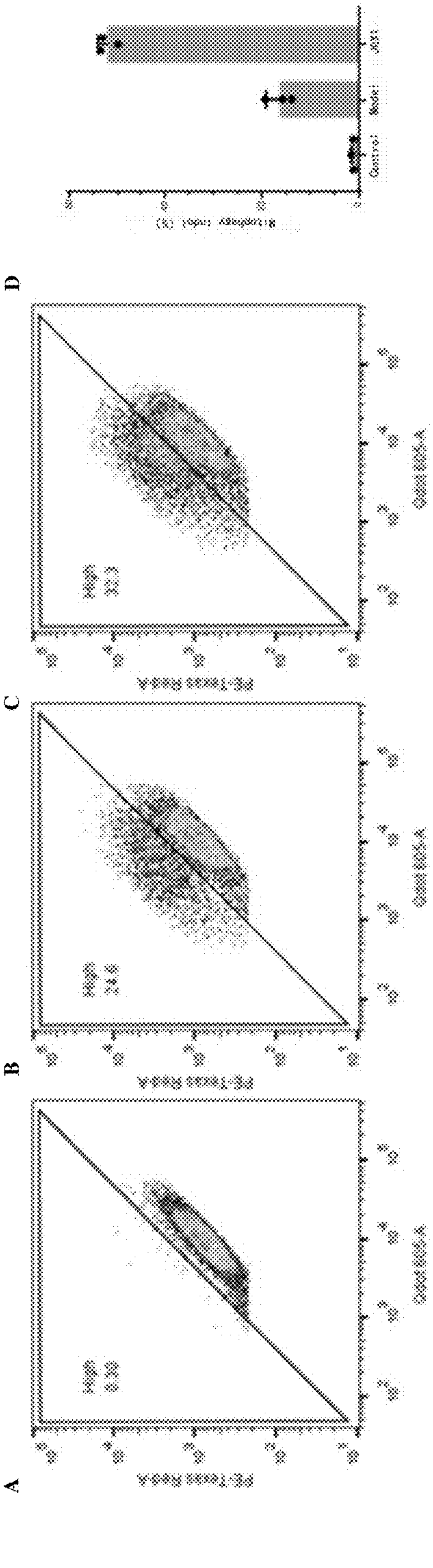
FIG. 1 shows the flow cytometry results of Crassifolin A (JGX-1) for screening a mitophagy drug, wherein A is the result of a DMSO group, B is the result of a positive control group (FCCP) (10 μM in concentration), and C is the result of a JGX-1 treatment group (10 μM in concentration), and D is a statistical histogram.

The results were shown in FIG. 1. Through screening mitophagy by flow cytometry, it was found that JGX-1 could enhance mitophagy.

(2) Detection of Mitophagy in Hela-Mt-Keima Cells by Using Confocal Microscopy

The Keima fluorescent protein derived from anthozoan has a pH value-dependent bimodal excitation spectrum, that is, Keima at neutral pH and acidic pH can be excited to emit green fluorescence and red fluorescence under the excitation of light with a wavelength of 440 nm and 586 nm, respectively. Since mitochondria that undergo autophagy eventually enter acidic lysosomes, Keima with the mitochondrial localization (mitochondrial Keima, mt-Keima) can indicate the mitochondria that enter the lysosomes via the autophagic pathway. The specific procedure of this experiment is as follows:

Inoculation of Hela-mt-Keima cells into 12 laser confocal cell culture dishes at a density of $1\times10^4$, and then adding 1 mL of DMEM medium containing 10% (v/v) FBS; after 5 h, changing the solution, and dividing into a solvent control group (DMSO), a positive drug control group (10 μM FCCP), an experimental group 1 (10 μM JGX-1+10 μM FCCP) and an experimental group 2 (10 μM JGX-1), with 3 replicates in each group; incubating cells in a 5% (v/v) $CO_2$ cell culture incubator at 37° C.; after 8 h, observing the changes in the excitation fluorescence signals of the 458 nm channel (indicating Keima at neutral pH) and the 561 nm channel (indicating Keima at acidic pH) under a laser confocal microscope, randomly selecting 3 fields of view to take photos, and then statistically plotting.

Figure 2:
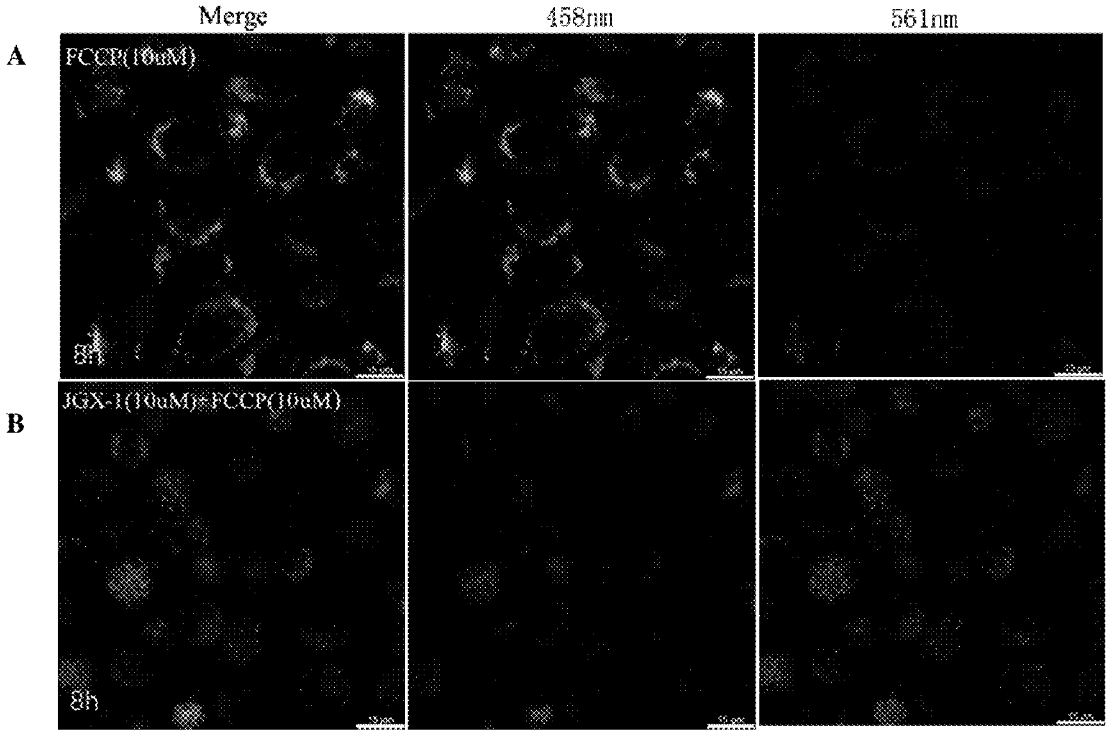
FIG. 2 shows the mitophagy situation observed under a laser confocal microscope after treatment of Hela-mt-Keima cells with Crassifolin A (JGX-1), wherein A is the situation of a positive control group (FCCP) (10 μM in concentration), and B is the situation of a JGX-1 treatment group (10 μM in concentration).

The results are shown in FIG. 2. Through confocal live cell imaging, it was found that JGX-1 could enhance mitophagy.

(3) Western Blot a. Treating hSY5Y cells with JGX-1 (10 μmol/L) for 24 h and then collecting the cells, and determining the protein concentration of the hSY5Y cell samples using the BCA method at a consistent sample loading amount (20 μg/10 μL);
b. formulating a separation gel and a spacer gel;
c. electrophoresis: adding 10 μL of sample to each hole, and carrying out electrophoresis at 80 V for 30 min; when the sample entered the separation gel, adjusting the voltage to 120 V, and carrying out electrophoresis for 60 min until the bromophenol blue entered the bottom of the separation gel;
d. transfer: using a wet transfer method, i.e., first activating a PVDF membrane with methanol 3 min in advance, then placing sponge, filter paper, gel, PVDF, filter paper, and sponge in turn from a negative electrode to a positive electrode, and then electro-transferring at low temperature for 90 min in a pre-cooled transfer buffer with a constant current of 300 mA, with the entire process being carried out in ice water;
e. after the transfer was completed, placing the membrane in a culture dish of 5% (w/v) skimmed milk powder prepared with a TBST buffer, then sealing at room temperature for 90 min, and then washing 3 times for 5 min each with the TBST buffer;
f. incubation of primary antibody: diluting primary antibodies LC3B and pTAU (202) (CST company) with a primary antibody diluent, incubating overnight at 4° C., and then washing 3 times for 10 min each on a shaker with an appropriate amount of the TBST buffer;
g. incubation of secondary antibody: diluting a secondary antibody HRP (CST company) with the TBST buffer, incubating for 1 h at room temperature, and then washing 3 times for 10 min each on a shaker with an appropriate amount of the TBST buffer; and
h. chemiluminescence reaction: dropping a fresh BeyoECLplus working solution (ultrasensitive ECL chemiluminescence kit) onto the membrane and ensuring the coverage of the membrane by the working solution, and then collecting fluorescence signals by using an instrument ALLIANCE 4.7.

Figure 3:
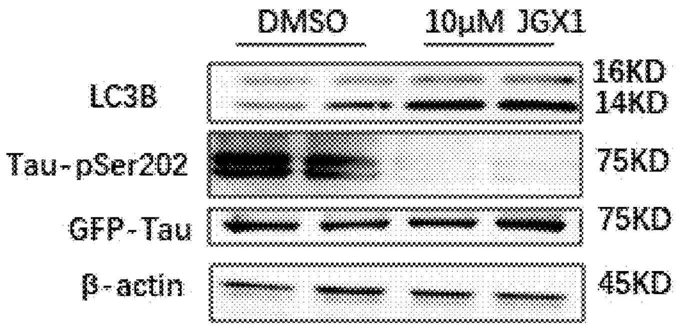
FIG. 3 shows the Westerning Blot results based on the analysis of the effect of treatment with Crassifolin A (JGX-1) on tau proteins in SH-SY5Y-Tau-GFP cells.

The results were shown in FIG. 3. It was verified by WB that JGX-1 enhanced the expression of autophagic LC3B and inhibited the expression of phosphorylated Tau in the hSY5Y cells.

(4) Detection of Learning Memory of Mice by Morris Water Maze Test a. Treating 10-month-old Tau model mice with oral administration of JGX-1 (20 mg/kg) for 3 consecutive months, and then carrying out the Morris water maze test after 3 months;
b. adding water to the water maze device to a water depth of 40 cm and keeping the water temperature at (22±1° C.), and then adding white non-toxic paint to the water, with a platform (10 cm in diameter) located 1.5 cm underwater in the third quadrant;
c. training the mice to find the platform separately from the middle of each of three quadrants (except the target quadrant) facing the pool wall alone for 7 consecutive days, 3 times a day, at an interval of 60 s; during the training phase, requiring the mice to find the platform within 60 s and to stay thereon for 15 s, and if the animals failed to find the platform within 60 s, recording the time as 60 s; and then guiding these mice onto the platform to stay thereon for 15 s; using a camera to automatically record the mice's swimming trajectory, time to reach the previously placed platform, swimming speed, and swimming distance; and
d. on the 8th day, removing the platform and placing the mice separately in the quadrant in a position opposite to the original platform; using the camera to automatically record the animals' swimming trajectory within 60 s, duration of stay in the quadrant where the platform was located, number of times they crossed the location of the platform, swimming speed, and swimming distance.

Figure 4:
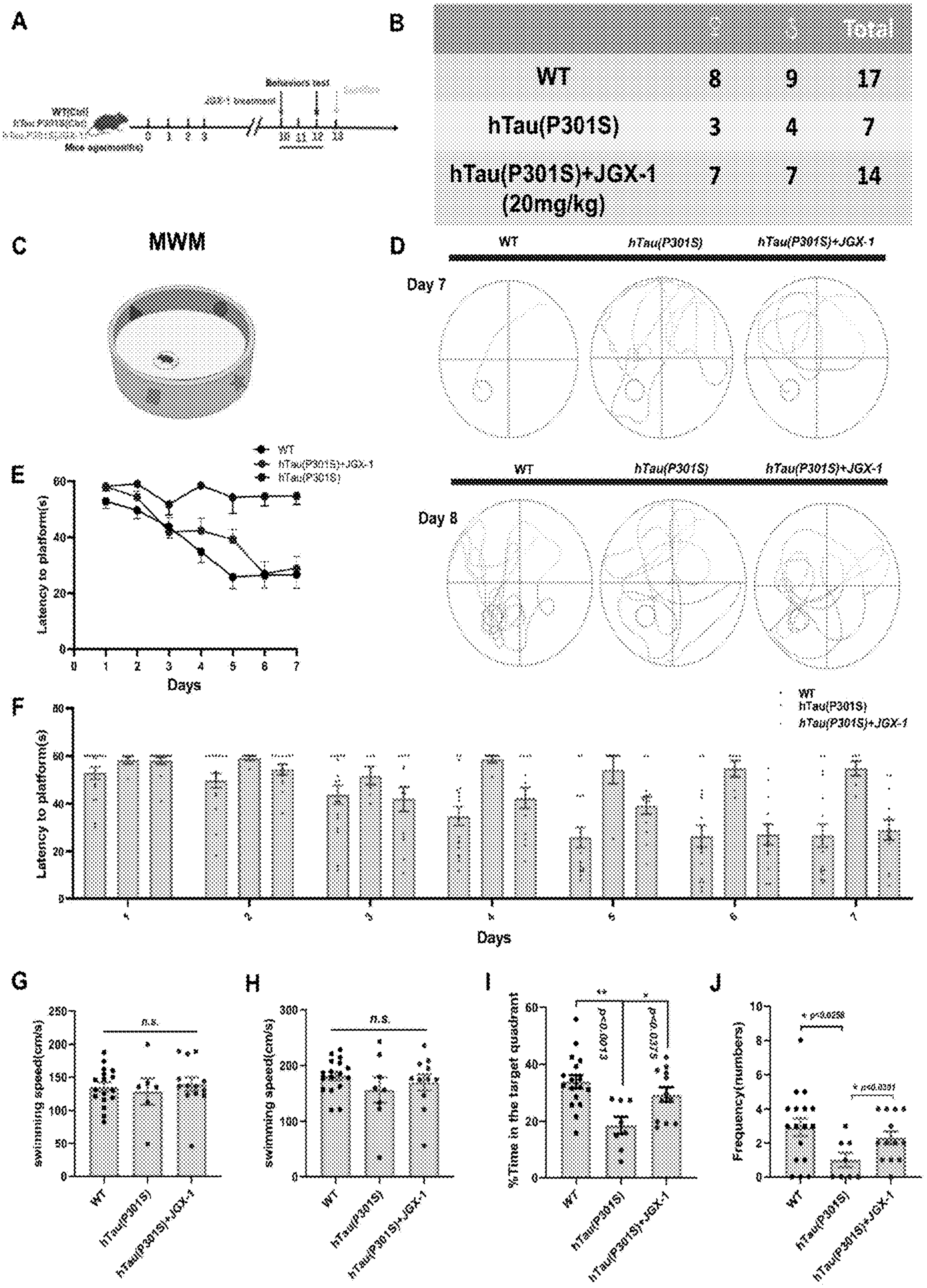
FIG. 4 shows the results of Morris water maze test for Crassifolin A (JGX-1) to improve the learning memory of AD model mice (Tau mice).

The results are shown in FIG. 4. The Morris water maze test showed that JGX-1 had an improved effect on the learning memory of AD model mice, alleviated the dementia symptoms in the model mice, and had a significant therapeutic effect.

The above Examples are preferred embodiments of the present invention, but the embodiments of the present invention are not limited thereto, and any other alterations, modifications, replacements, combinations and simplifications made without departing from the spirit and principle of the present invention shall all be equivalent substitution modes and included in the scope of protection of the present invention.

The invention claimed is:

1. A method for promoting cellular mitophagy in vitro, comprising providing an effective amount of Crassifolin A to cultured human cells, wherein the Crassifolin A has the following chemical structural formula as shown in Formula (I):

Formula (I)

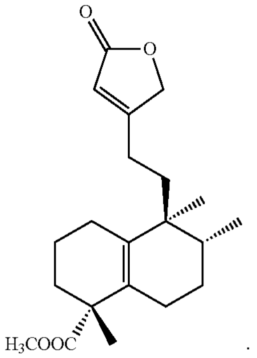

2. The method according to claim 1, wherein the effective concentration of the provided Crassifolin A is 5-15 μmol/L.

3. The method according to claim 2, wherein the effective concentration of the provided Crassifolin A is 10 μmol/L.

4. A method for treatment of a neurodegenerative disease, comprising administering to a subject an effective amount of Crassifolin A, wherein the Crassifolin A has the following chemical structural formula as shown in Formula (I):

Formula (I)

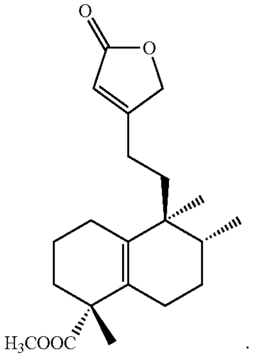

thereby treating the neurodegenerative disease.

5. The method according to claim 4, wherein the the Crassifolin A promotes mitophagy and inhibits expression of phosphorylated Tau, thereby treating the neurodegenerative disease.

6. The method according to claim 4, wherein the neurodegenerative disease is selected from the group consisting of Alzheimer's disease, Parkinson's disease, Huntington's disease, amyotrophic lateral sclerosis, a spinal cerebellar ataxia, Pick's disease, cerebral ischemia, brain injury, and epilepsy.

* * * * *